(12) United States Patent
Marrone

(10) Patent No.: US 11,535,586 B2
(45) Date of Patent: Dec. 27, 2022

(54) PROCESS FOR THE SYNTHESIS OF UREA

(71) Applicant: Casale SA, Lugano (CH)

(72) Inventor: Leonardo Marrone, Mercallo (IT)

(73) Assignee: Casale SA, Lugano (CH)

( * ) Notice: Subject to any disclaimer, the term of this patent is extended or adjusted under 35 U.S.C. 154(b) by 71 days.

(21) Appl. No.: 17/287,895

(22) PCT Filed: Nov. 7, 2019

(86) PCT No.: PCT/EP2019/080471
§ 371 (c)(1),
(2) Date: Apr. 22, 2021

(87) PCT Pub. No.: WO2020/104197
PCT Pub. Date: May 28, 2020

(65) Prior Publication Data
US 2021/0395190 A1    Dec. 23, 2021

(30) Foreign Application Priority Data
Nov. 22, 2018    (EP) .................................... 18207697

(51) Int. Cl.
| C07C 273/16 | (2006.01) |
| B01J 19/24 | (2006.01) |
| C07C 273/04 | (2006.01) |
| B01D 1/22 | (2006.01) |
| B01D 9/00 | (2006.01) |

(52) U.S. Cl.
CPC .............. *C07C 273/16* (2013.01); *B01D 1/22* (2013.01); *B01D 9/00* (2013.01); *B01J 19/2465* (2013.01); *C07C 273/04* (2013.01); *B01D 2009/0086* (2013.01); *B01J 2219/00024* (2013.01); *B01J 2219/00108* (2013.01); *B01J 2219/00162* (2013.01)

(58) Field of Classification Search
None
See application file for complete search history.

(56) References Cited

U.S. PATENT DOCUMENTS 5,523,483 A * 6/1996 Singh .................... C07C 273/04
564/69
2017/0152218 A1 * 6/2017 Ostuni .................. C07C 273/04

FOREIGN PATENT DOCUMENTS

| EP | 2505581 A1 | 10/2012 |
| GB | 1173195 A | 12/1969 |
| WO | 2013/104638 A1 | 7/2013 |
| WO | 2014/122894 A1 | 8/2014 |

OTHER PUBLICATIONS

International Preliminary Report on Patentability issued in connection with PCT/EP2019/080471, dated Nov. 11, 2020.
International Search Report issued in connection with PCT/EP2019/080471, dated Jan. 14, 2020.

* cited by examiner

*Primary Examiner* — Amy C Bonaparte
(74) *Attorney, Agent, or Firm* — Akerman LLP

(57) ABSTRACT

A process for synthesis of urea from $CO_2$ and $NH_3$ wherein a steam flow (13) produced in the condenser (3) of a high-pressure synthesis loop is compressed to raise its pressure and temperature before using the steam as a heat source for a downstream step of the process.

21 Claims, 3 Drawing Sheets

PROCESS FOR THE SYNTHESIS OF UREA

CROSS-REFERENCE TO RELATED APPLICATIONS

This application is a national phase of PCT/EP2019/080471, filed Nov. 7, 2019, and claims priority to EP 18207697.6, filed Nov. 22, 2018, the entire contents of both of which are hereby incorporated by reference.

FIELD OF THE INVENTION

The invention relates to the field of urea production. The invention relates in particular to a process and plant including a reactor, a stripper and a condenser in a high-pressure loop.

PRIOR ART

Urea is synthesized by reacting ammonia and carbon dioxide. A discussion of the various processes and related plants for the urea production can be found in literature, e.g. Ullmann's Encyclopaedia of Industrial Chemistry, Wiley-VCH Verlag.

Most urea plants nowadays use a so-called stripping process. In a stripping process, a carbamate-containing aqueous solution of urea effluent from a reactor is processed in one or more steam-heated stripper(s), where the carbamate is decomposed to $CO_2$ and $NH_3$; a purified urea solution taken from the stripper is further treated in one or more recovery section(s) at a medium pressure and/or at a low pressure; a gaseous phase containing ammonia, carbon dioxide and a small amount of water emerging from the stripper is sent to a condenser and the so obtained condensate is recycled to the reactor.

The stripper may be fed with a stripping medium to promote the process of stripping. The stripping medium is normally gaseous carbon dioxide or gaseous ammonia. The $CO_2$-stripping process introduced by Stamicarbon uses gaseous carbon dioxide fed to the stripper as a stripping medium. The Snamprogetti ammonia- and self-stripping processes use gaseous ammonia as a stripping aid (ammonia-stripping) or achieve stripping only by use of heat (self-stripping).

The reactor, the stripper and the condenser are part of a so-called high-pressure (HP) loop, wherein the pressure is generally in the range of 100 to 250 bar.

A recovery section comprises basically a decomposer, a liquid/gas separator and a condenser. In the decomposer, the urea solution is heated to decompose the ammonium carbamate and vaporize ammonia and carbon dioxide as well as water. The so obtained purified solution can be sent to a further recovery section, if provided, or to a final concentration stage. A carbamate solution formed in the condenser returns to the high pressure synthesis loop. A medium-pressure (MP) recovery section generally operates at 18-20 bar; a low-pressure (LP) recovery section generally operates at 2 to 6 bar.

An advantage of the stripping process is that most of the heat furnished to the stripper, to decompose the carbamate, can be recovered in the high-pressure condenser, producing steam. For example the HP condenser can be a shell-and-tube equipment where a cooling water evaporates in the tubes to produce steam. The steam produced in the high-pressure condenser can be advantageously used as a heating medium for one or more section(s) downstream, for example in a recovery section and/or in an evaporation section.

In a $CO_2$-stripping process, the items of said HP loop normally operate at substantially the same pressure (isobaric loop). The ammonia-stripping and self-stripping processes use a near-isobaric loop wherein the HP stripper is operated at a pressure lower than the reaction pressure, the difference between the reaction pressure and stripping pressure being however a relatively small difference, typically not greater than 20 bar (i.e. about 10%-15% of the reaction pressure).

In the above cases, the working pressure of the reactor, the stripper and the condenser is the result of a compromise. A high temperature and high pressure in the synthesis loop promotes the conversion of ammonium carbamate into urea (endothermic reaction limited by the thermodynamic equilibrium) in the reactor; on the other hand a low pressure (e.g. less than 100 bar) helps the stripping process and may avoid the need of a MP recovery section. It is thus desirable to have a synthesis loop that maximizes the reactor temperature and minimizes the pressure of the HP stripper.

An isobaric or near-isobaric loop is not able to reaches this target. Another drawback of most plants using a $CO_2$-stripping isobaric loop is that the items must be installed at a certain minimum elevation to allow a circulation by gravity of the liquid phase. Particularly, it may be necessary to locate the reactor above the stripper to generate a driving force within the high-pressure synthesis loop.

To solve the above drawbacks, it has been proposed a $CO_2$ stripping plant with a non-isobaric loop wherein the HP stripper and the HP condenser run at a pressure significantly lower than the pressure of the synthesis reactor, for example the reactor runs at more than 150 bar and the stripper and condenser run at around 90 bar.

This solution allows optimization of the reaction pressure and stripping/condensation pressure, however it introduces another drawback in that it lowers the value of the heat recoverable from the condenser; more specifically it reduces the temperature and pressure of the steam that can be produced in the condenser. The steam produced in a condenser at said pressure of around 90 bar may not be suitable for use in the downstream process steps, e.g. in the recovery section. Accordingly, the solution of non-isobaric loop is not attractive because it reduces the heat that can be internally recovered and, consequently, the energy efficiency.

A field of great interest is also the revamping of the existing urea plants. A revamping of an existing plant is generally performed to increase the capacity (i.e. the amount of urea that can be produced) and/or to reduce energy consumption. Major sources of cost in a revamping procedure include the modification of high-pressure equipment and the provision of additional heat exchange surfaces. Even a relatively small increase of capacity may require the addition of a significant heat exchange surface, for example in the HP condenser, in a medium or low pressure recovery section, or in an evaporation section. This requires also a significant downtime of the production process.

SUMMARY OF THE INVENTION

The purpose of this invention is to overcome the above described drawbacks of the prior art. Particularly, a purpose of the invention is to optimize the operation of the high-pressure loop while maintaining an efficient recovery of heat for use in the downstream sections. Another aim of the invention is to provide a cost-effective method for revamping a urea plant, suitable to increase the capacity of the urea plant reducing the cost for additional heat exchange surface.

This purpose is reached with a process for synthesis of urea from $CO_2$ and $NH_3$ at high pressure, comprising:

a) reacting $CO_2$ and $NH_3$ at a reaction pressure to form an aqueous solution of urea;

b) stripping said aqueous solution of urea at a stripping pressure obtaining a purified solution and a gaseous phase containing ammonia and carbon dioxide;

c) condensing said gaseous phase in at least one condenser at a condensation pressure to form a recycle solution which is sent back to the reaction step, thus forming a synthesis loop;

d) producing at least a first steam flow at a first recovery pressure and first recovery temperature using heat removed from said gaseous phase during the condensation step c);

e) using said first steam flow as a heat source in at least one downstream step of the process, the process being characterized by:

f) a compression of said first steam flow to reach a pressure greater than said recovery pressure and a temperature greater than said recovery temperature, before said use as a heat source in at least one downstream step.

Preferably, the stripping step involves passing said aqueous solution as a falling film in an externally heated tube bundle. Accordingly, a stripper may include a falling-film vertical tube bundle. For example the tube bundle is steam-heated.

In some embodiments, the step d) may include producing more than one steam flow. The pressure and temperature of any additional steam flow may be the same as the first steam flow, or different. The step f) may include the compression of one or more additional steam flow, according to various embodiments. Accordingly, the steam which is subjected to compression may include the full amount of steam produced in the condensation step, or a portion thereof. For example the steam which is subjected to compression may include one or more selected steam flows, when a plurality of steam flows are generated, and/or a portion of a steam flow.

In some embodiments, the step d) may include the generation of different steam flow in separate high pressure carbamate condensers (HPCCs). For example the high pressure loop may comprise two HPCCs and said first steam flow is generated in one of the two condensers. In a preferred embodiment, the step d) includes the generation of said first steam flow and of a second steam flow in a first HPCC and a second HPCC respectively, said first HPCC and second HPCC being connected in series.

In a preferred application, said stripping pressure and said condensation pressure are lower than the reaction pressure, the synthesis loop being then non-isobaric. In a particularly preferred embodiment, the stripping pressure and the condensation pressure are at least 50 bar lower than the reaction pressure, more preferably at least 100 bar lower.

In the non-isobaric embodiments, the recycled solution may be obtained from condensation at a pressure significantly lower than the reaction pressure, thus requiring pressurization for recycling to the reaction environment. Preferably said solution is pumped to the reaction pressure by means of a centrifugal pump.

In a preferred embodiment, said first recovery pressure is 1.8 to 3.5 barg and said first steam flow is compressed to a pressure of 3.0 barg to 6.0 barg.

The symbol barg denotes bar gauge, i.e. the pressure relative to atmospheric pressure.

The compression of the steam also results in increase of temperature of the steam. The increase of the steam temperature through the compression step is preferably 10 to 30° C. Said first recovery temperature is preferably not greater than 145° C. and the steam after compression has preferably a temperature of at least 150° C.

The compression of the steam is preferably adiabatic or substantially adiabatic. The compression may be a multi-stage compression.

In a particularly preferred embodiment, said condensation pressure is 70 to 90 bar, preferably 80 bar or about 80 bar.

In a non-isobaric loop, the stripping may be performed at the same or at different pressure than the condensation. Preferably the stripping pressure is the same as the condensation pressure.

As stated before, a high reaction pressure is generally preferred to increase the conversion rate. In the preferred embodiments, the reaction pressure is greater than 140 bar and preferably greater than 200 bar.

The at least one downstream process step, where steam produced during the high-pressure condensation is used as a heat source, may include recovery of non-converted carbamate and/or concentration to remove water from a urea solution.

For example recovery of non-converted carbamate may be performed in a recovery section at a medium pressure or lower pressure, including a decomposer heated with the steam produced in the high-pressure condenser.

Concentration can be performed, for example, in an evaporation section downstream the one or more recovery section(s), wherein water is removed to form a highly concentrated urea melt suitable for a finishing process, such as prilling or granulation.

A process of concentration may also be performed in a crystallization section. The crystallization process is known and involves that the urea product is partially crystallized and the formed vapor in a crystallizer is condensed while the urea solution including the formed urea crystals leaving the crystallizer is subjected to a liquid solid separator. The bulk of solution is separated from the urea crystals and the crystals are then subjected to a centrifuge, wherein the urea crystals are washed using a mother liquor comprising a urea water solution.

A crystallization section may run using a low-grade steam. A steam which is not compressed after generation can be advantageously used to heat a crystallization section. This means that the use of a crystallization process for concentration of the urea section has the advantage of reducing the amount of steam to be mechanically compressed. Accordingly, in an embodiment of the invention, the step d) further includes the generation of at least a second steam flow, which is not compressed after generation, and is used to provide heat to a crystallization section for the concentration of a urea solution.

The stripping of the solution can be performed with the aid of a gaseous stripping medium. For example $CO_2$ or ammonia can be used as stripping medium. In some embodiments of the $CO_2$-stripping process, a fresh feed of gaseous $CO_2$ is partly directed to the stripper, for use as a stripping aid, and partly directed to the reactor.

In a preferred embodiment, no part of the fresh CO2 feed is directly sent to the condenser. Accordingly the fresh CO2 may be sent to the reactor and possibly, in case of a CO2-stripping process, may be sent partly to the stripper.

The high-pressure loop may comprise more than one condensation steps, for example in two HPCCs in series. In an interesting embodiment, a biphasic solution produced in a first condensation step is subjected to at least one second condensation step. In the second condensation step, a saturated steam may be produced. Said saturated steam can advantageously be used for pre-heating the ammonia feed and/or in a pre-concentration step of the urea solution leaving the recovery section. Alternatively it can also be used to remove water in a concentration section based on the crystallization technology.

In some embodiments, a biphasic solution produced in a first condensation step can be used directly as heating medium in the ammonia preheater and/or in some of the decomposers of the recovery section and/or in the concentration section.

In a preferred embodiment, the compression of the steam is performed with an electric compressor, i.e. a compressor driven by an electric motor, instead of the conventional compressor driven by a steam turbine. Particularly in case of a revamping, the installation of an electric compressor can be economically advantageous over the conventional compressors coupled to a steam turbine (turbo-compressors). The applicant has found that, surprisingly, the installation of an electrical compressor can reduce the overall consumption of a urea plant in terms of GCal per metric tons of urea produced.

A further aspect of the invention is a plant according to the claims.

A further aspect of the invention is a method for revamping a urea plant wherein the plant comprises:

a reactor where $CO_2$ and $NH_3$ react at a reaction pressure to form an aqueous solution of urea;

a stripper fed with said aqueous solution of urea, wherein the solution is treated at a stripping pressure obtaining a purified solution and a gaseous phase containing ammonia and carbon dioxide;

a condenser for condensing said gaseous phase from the stripper at a condensation pressure to form a recycle solution which is sent back to the reactor, thus forming a synthesis loop;

a steam system comprising a steam line arranged to produce at least a first steam flow using heat removed from the condenser, wherein said first steam flow is used as a heat source in at least one downstream section of the plant;

and the method includes:

adding a steam compressor to said steam system, the added compressor being arranged to raise the pressure of said first steam flow.

Upon installation of the added steam compressor, the compressed steam flow is delivered to said at least one downstream section. This can be made with a new steam line or an existing steam line.

The method of revamping according to the invention is applicable to urea plants with an isobaric or non-isobaric synthesis loop. The method is applicable among others to $CO_2$-stripping, self-stripping and ammonia-stripping plants.

The main advantage of the invention is that the pressure and temperature of the steam made available by the high-pressure condenser for use in the downstream equipment is no longer dictated by the condensation pressure and related steam recovery pressure. According to the invention, one or more steam flows generated by condensation are compressed and delivered to thermal users to a pressure and temperature greater than condenser outlet. The temperature of the heat which is internally recycled from the high-pressure condensation toward a medium- or low-pressure stage is not dictated by the choice of the condensation pressure in the high-pressure carbamate condenser.

It can be said that the invention implements a heat pump between the high-pressure loop and a medium- or low-pressure section downstream, where the steam is used as a heat source for one or more thermal users. This heat pump takes a thermal energy released by the condenser at a first temperature (e.g. a steam generated at 135° C.) and transfers this energy to the target section at a higher temperature (e.g. steam condensing at 150° C.).

Therefore, the condensation pressure can be selected to optimize the condensation process and the stripping process, the latter being preferably performed at the same pressure. On the other hand, a selection of a relatively low condensation pressure (e.g. 80 bar) does not affect the internal heat recovery toward the downstream sections, thanks to the compression of the steam produced in the HPCC.

It can be noted that the compression requires an input of energy; however in practical cases the compression ratio is small (typically less than 2) which means the coefficient of performance (COP) of said heat pump is quite high, for example 10 or more. In some embodiments the COP of said heat pump is about 20.

The above mentioned COP denotes the ratio of the heat released over the work for compression.

Another advantage of the invention is the reduced need of maintenance of the items. Running the stripping and condensation steps at 70-90 bar and consequent lower temperature, implicates a reduction of the corrosive effect of the ammonium carbamate on the equipment. Moreover, the potential formation of side products such as biuret during the HP decomposition step is reduced, leading to a higher quality of the final product urea. Another advantage is the reduced hydrolysis of urea due to the lower temperature in the HP decomposer.

Still another advantage of the invention is that, for a given condensation temperature on the process side, the recovery pressure of the generated steam can be reduced to enhance the heat exchange performance for a given heat exchange surface of the condenser. The lower temperature of the so obtained steam does not affect the subsequent recovery thanks to the intermediate compression and heating of the steam.

The invention is also interesting for the revamping of a urea plant. The invention can be applied to the revamping of urea plant with a isobaric or non-isobaric high-pressure loop. The advantages of a revamping according to the invention include: the possibility to achieve a small but significant increase of capacity without a modification of the existing HPCC and existing MP or LP decomposers and/or evaporators; short time of plant shutdown; limited investment cost. The increase of the capacity is obtained by providing an additional difference of temperature (ΔT) to the HPCC and to the decomposers of the MP or LP section, thus increasing the amount of heat that can be transferred keeping constant the area of thermal exchange.

The invention is applicable to various urea processes, particularly to the known $CO_2$ stripping process and self-stripping process. In both cases the invention provides a reduced steam consumption compared to the original technology.

One of the advantages of the invention is reducing the energy consumption. For example the applicant has found that the invention may reduce consumption by 0.1 Gcal/MT (Gcal per metric tonne of urea) in a self-stripping process and by 0.12 Gcal/MT in a self-stripping process.

DETAILED DESCRIPTION

Figure 1:
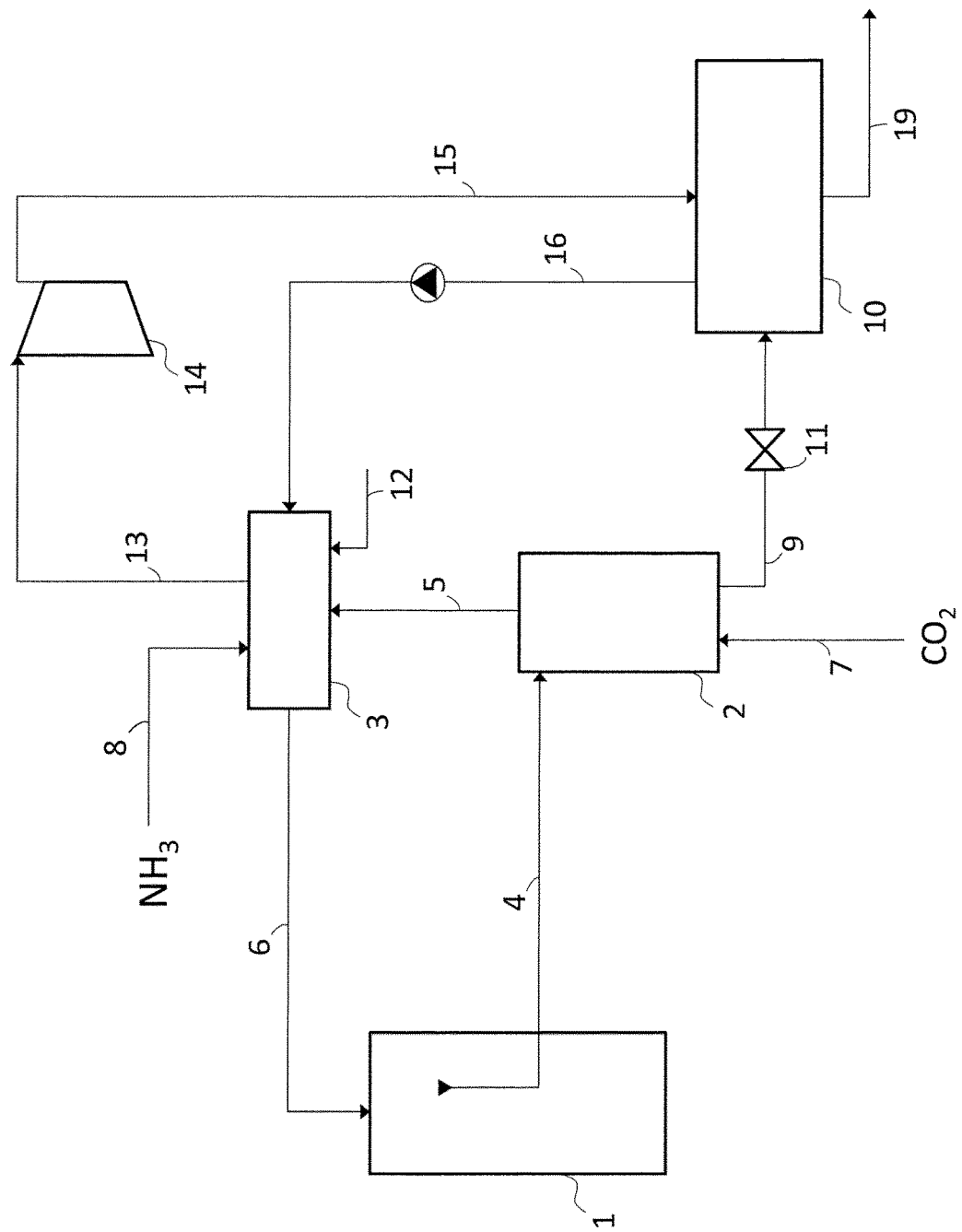
FIG. 1 is a scheme of a $CO_2$ stripping urea plant revamped according to a first embodiment of the invention.

FIG. 1 illustrates in a simplified manner a conventional $CO_2$ stripping urea synthesis loop comprising a reactor 1, a stripper 2 and a condenser 3 which operate substantially at the same pressure, for example at 120 to 210 bar. Accordingly, said reactor 1, stripper 2 and condenser 3 form an isobaric HP loop. The loop may comprise additional items (e.g. a scrubber) which are not illustrated.

A fresh $CO_2$ stream 7 is fed to the stripper 2 and a feed of $NH_3$ 8 is fed to the condenser 3, for example with an ejector (not shown). In a further embodiment of the invention the feed of fresh $CO_2$ can be separated in two streams feeding the reactor 1 and the stripper 2 (not shown).

The $CO_2$ stream 7 acts as a stripping medium in the stripper 2.

An aqueous solution 4 containing urea and carbamate formed in the reactor 1 is sent to the stripper 2, where a purified urea solution 9 and a gaseous phase 5 are obtained.

The purified urea solution 9 is sent to one or more recovery stage(s), for example at a recovery section 10 at low pressure (for example 2-6 bar) passing through an expansion valve 11.

In the recovery section 10, the urea solution 9 after decompression is subjected to further treatments including decomposition of carbamate and condensation of vapours of ammonia and carbon dioxide. A so obtained solution of carbamate 16 is pumped back to high-pressure condenser 3. A purified urea solution 19 is sent to a downstream finishing section.

The gaseous phase 5 from the stripper 2 is at least partially condensed in the condenser 3 and recycled via line 6 to the reactor 1.

In the condenser 3, the heat of condensation of the gaseous phase 5 is transferred to water 12 and used to produce steam 13 for use in a downstream section of the plant, for example in the recovery section 10, as illustrated in the FIG. 1, or in a finishing section after the recovery section 10.

Particularly, the steam 13 produced in the condenser 3 is compressed in a steam compressor 14 to raise its pressure and temperature. The so obtained compressed/heated steam 15 delivered by said compressor 14 may be directed to the recovery section 10 where it provides heat to one or more related equipment, for example to one or more decomposer(s) operating at a medium pressure and/or at a low pressure.

The steam compressor 14 may be a multi-stage compressor. In some embodiments, the steam compressor 14 is an electric compressor.

In another embodiment, at least part of the steam 15 may be used in a finishing section after the recovery section 10. Said finishing section may include an evaporation section or a crystallization section to remove water from the solution 19. The hot steam 15 may be used for example to furnish heat to the evaporation section or to the crystallization section.

Figure 2:
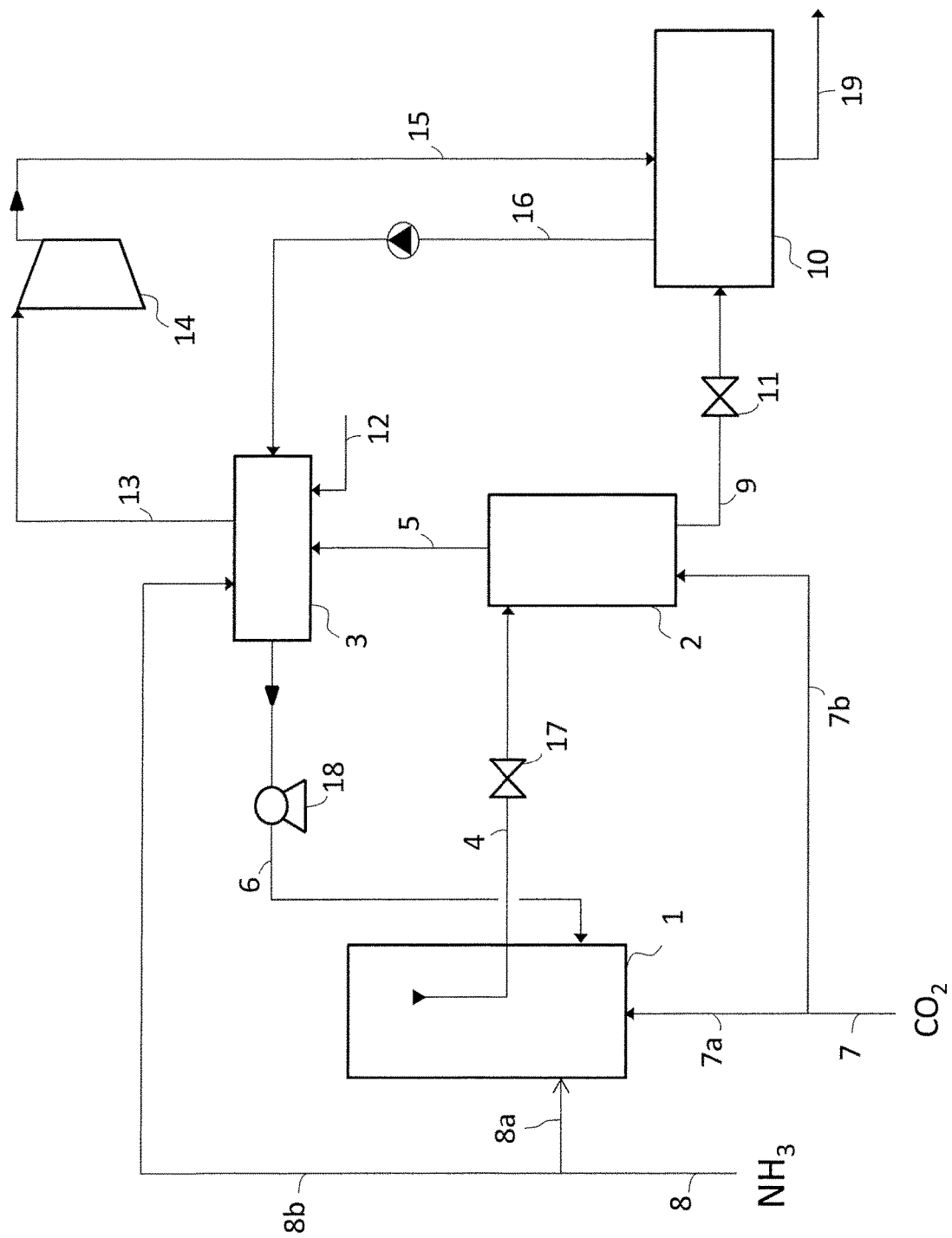
FIG. 2 is a scheme of a $CO_2$ stripping urea plant according to a second embodiment of the invention.

FIG. 2 illustrates a $CO_2$ stripping plant in accordance with a second embodiment where items corresponding to FIG. 1 are denoted by the same numerals.

In FIG. 2 the high-pressure loop formed by the reactor 1, stripper 2 and condenser 3 is non-isobaric. In particular, the stripper 2 and condenser 3 operate at a pressure lower than the pressure of reactor 1. For example, the reactor 1 operates at 210 bar while the stripper 2 and condenser 3 operate at around 80 bar.

The reaction effluent 4 is de-compressed to the stripping pressure through a valve 17 and the recycle solution withdrawn from the condenser 3 is brought to reaction pressure through a pump 18.

An advantage of the embodiment of FIG. 2 is that the stripper and condenser can be operated at relatively low pressure, compared to the reaction pressure; the heat recovery from the condenser 3 to the recovery section 10 is however not penalized by the relatively low condensation pressure, thanks to the intermediate compression through the compressor 14. This compression raises the temperature of the steam, thus making the steam 15 useful for heating the recovery section 10, e.g. a decomposer of the same.

Also in the embodiment of FIG. 2, the fresh $CO_2$ feed 7 may be split in two streams 7a and 7b directed respectively to the reactor 1 and to the stripper 2 as illustrated.

The fresh ammonia 8 is split into stream 8a directed to the reactor 1 and stream 8b directed to the condenser 3.

The compressor 14 implements a heat pump transferring heat from the condenser 3 to the recovery section 10 while raising the temperature of said heat.

In a preferred embodiment, the steam 13 produced by the condenser 3 has a temperature of around 135° C. and a pressure of around 2.1 barg; the steam 15 delivered by the compressor 14 has a temperature at least of 150° C. and a pressure of above 3.5 barg.

In further advantageous embodiments of the invention, the high-pressure loop may comprise more than one condenser. For example, in a urea synthesis process including a non-isobaric high-pressure loop, a biphasic solution produced in the condenser 3 is subjected to a second condensation step, wherein a saturated water steam is produced. Said saturated steam can be used to pre-heat the ammonia and/or in a pre-concentration step of the solution 19, before the solution is fed to an evaporation section to remove water and produce a urea melt. Alternatively it can be also used to remove water in a concentration section based on the crystallization technology.

Said pre-concentration step may be carried out for example in a shell-and-tube pre-concentrator by sending the biphasic solution to the shell side.

Figure 3:
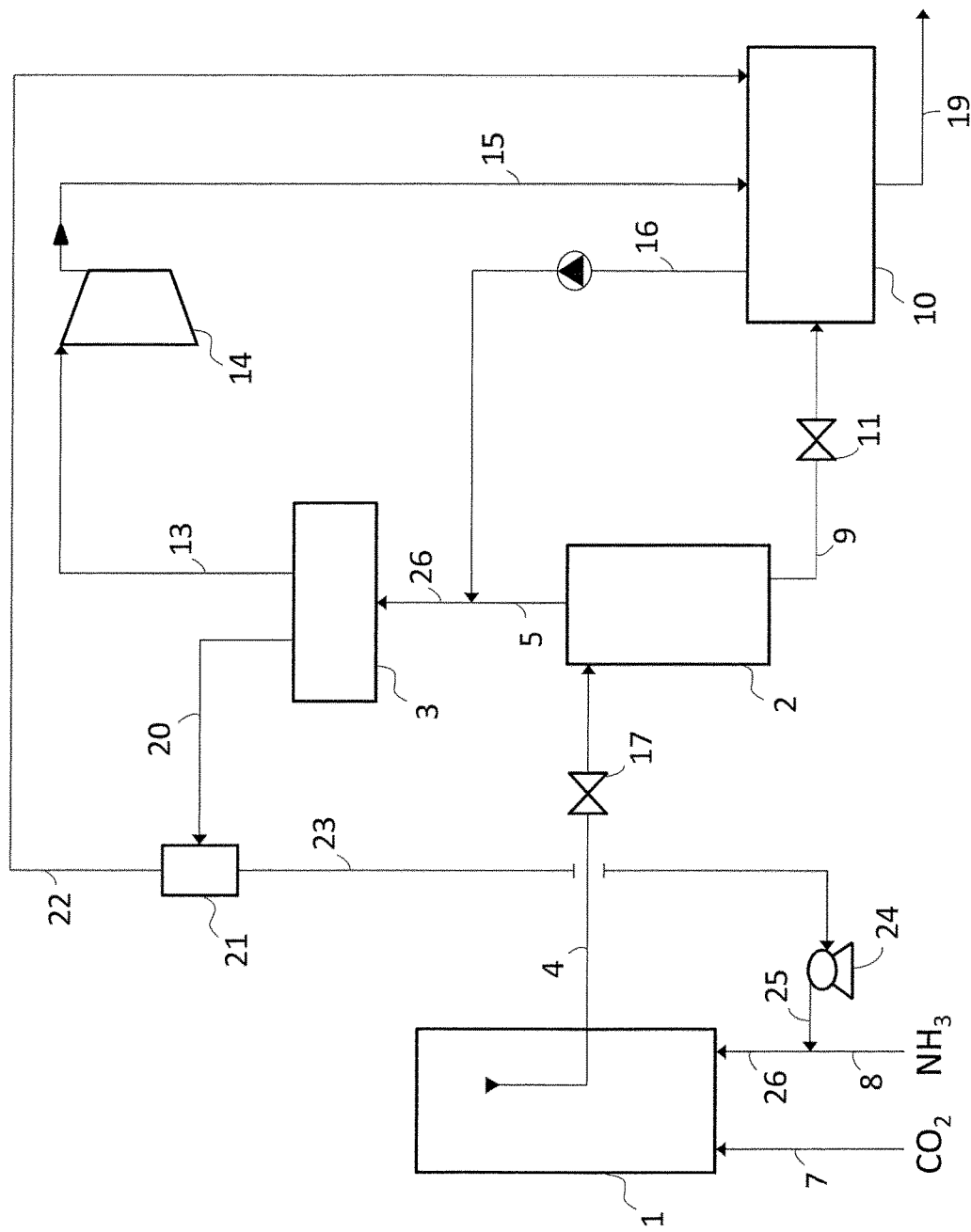
FIG. 3 is a scheme of a self-stripping urea plant according to a third embodiment of the invention.

FIG. 3 is a scheme of a self-stripping urea plant comprising a reactor 1, a stripper 2 and a condenser 3.

A fresh $CO_2$ stream 7 and a feed of $NH_3$ 8 are fed to the reactor 1. The reactor effluent 4 is depressurized through a valve 17 and sent to the stripper 2. After the stripping process, a purified urea effluent 9 is sent to one or more recovery section(s) 10 downstream by passing through an expansion valve 11. Typically the recovery sections include a medium-pressure recovery section and a low-pressure recovery section. After treatment in the recovery sections, a purified solution 19 is then sent to a finishing section.

The gaseous phase 5 formed during the self-stripping step is combined with the carbamate recycle solution 16 from the recovery sections. The so obtained stream 26 is at least partially condensed in the condenser 3 and the condensed carbamate solution 20 is sent to a carbamate separator 21, wherein a liquid solution 23 and a gaseous phase 22 are produced.

The liquid solution 23 is recycled to the reactor 1 by means of a pump 24 which brings the solution 23 back to the reaction pressure. Before reaching the reactor 1, the liquid solution 25 delivered by the pump 24 is combined with the ammonia fresh feed 8 from outside to form a flow 26. The flow 26 is then sent to the reactor 1.

The gaseous phase 22 produced in the carbamate separator 21 is sent to the recovery section, for example to a medium-pressure decomposer.

In a variant of FIG. 3, the stripper 2 and condenser 3 may operate at a pressure which only slightly less than the reaction pressure. In this case the solution 23 can be fed to the reactor 1 with an ejector (instead of pump 24) wherein the motive stream of the ejector is the ammonia feed 8.

The schemes of FIGS. 1 to 3 may result from the revamping of an existing plant, wherein the revamping includes the addition of the compressor 14 and if necessary the provision of the related steam line.

What is claimed is:

1. A process for synthesis of urea from $CO_2$ and $NH_3$ comprising:
   a) reacting $CO_2$ and $NH_3$ at a reaction pressure to form an aqueous solution of urea;
   b) stripping said aqueous solution of urea at a stripping pressure obtaining a purified solution and a gaseous phase containing ammonia and carbon dioxide, wherein the stripping step involves passing said aqueous solution as a falling film in an externally heated tube bundle;
   c) condensing said gaseous phase in at least one condenser at a condensation pressure to form a recycle solution which is sent back to the reaction step, thus forming a synthesis loop;
   d) producing at least a first steam flow at a first recovery pressure and first recovery temperature using heat removed from said gaseous phase during the condensation step c);
   e) using said first steam flow as a heat source in at least one downstream step of the process,
   wherein:
   f) a compression of said first steam flow to reach a pressure greater than said recovery pressure and a temperature greater than said recovery temperature, before said use as a heat source in the at least one downstream step,
   wherein no fresh $CO_2$ is added during the condensation step and wherein said step of compression of said first steam flow is performed with a compressor driven by an electric motor.

2. The process according to claim 1, wherein the stripping pressure and the condensation pressure are lower than the reaction pressure, the synthesis loop being then non-isobaric.

3. The process according to claim 2, wherein the stripping pressure and the condensation pressure are at least 20 bar lower than the reaction pressure.

4. The process according to claim 1, wherein said condensation pressure is 70 to 90 bar.

5. The process according to claim 1, wherein said stripping pressure is the same as the condensation pressure.

6. The process according to claim 1, wherein the compression of said step f) is performed with a compression ratio not greater than 2.

7. The process according to claim 1, wherein said first recovery pressure is 1.8 to 4.0 barg and the steam after compression of step f) has a pressure of 3 barg to 6 barg.

8. The process according to claim 1, wherein said first recovery temperature is not greater than 145° C. and the steam after compression of step f) has a temperature of at least 150° C.

9. The process according to claim 1, wherein the step d) includes the generation of at least two steam flows at different pressures and at least one of said steam flows is compressed according to step f).

10. The process according to claim 1, wherein the reaction pressure is greater than 140 bar.

11. The process according to claim 1, including the use of the compressed steam as a heat source in any of:
    a step of recovery of non-converted carbamate;
    a step of evaporation to remove water from a urea solution; and
    a step of crystallization to remove water from a urea solution.

12. The process according to claim 1, wherein the stripping of the solution is performed with the aid of a gaseous stripping medium and said stripping medium is $CO_2$ or ammonia.

13. The process according to claim 1, wherein the step d) further includes the generation of at least a second steam flow, which is not compressed after generation, and is used to provide heat to a crystallization section for the concentration of a urea solution.

14. The process according to claim 2, wherein said recycle solution, which is obtained from condensation, is pumped to the reaction pressure by means of a centrifugal pump.

15. A plant for synthesis of urea from $CO_2$ and $NH_3$ comprising at least:
    a reactor where $CO_2$ and $NH_3$ react at a reaction pressure to form an aqueous solution of urea;
    a stripper fed with said aqueous solution of urea, wherein the solution is treated at a stripping pressure obtaining a purified solution and a gaseous phase containing ammonia and carbon dioxide, wherein the stripper includes a falling-film vertical tube bundle;
    a condenser for condensing said gaseous phase from the stripper at a condensation pressure to form a recycle solution which is sent back to the reactor, thus forming a synthesis loop;
    a steam system comprising at least a first steam line arranged to produce a first steam flow using heat removed from the condenser, wherein said first steam flow is used as a heat source in at least one downstream section of the plant;
    wherein:
    said steam system comprises a steam compressor arranged to raise the pressure of said first steam flow and deliver the so obtained compressed steam flow to said at least one downstream section, wherein said steam compressor is driven by an electric motor.

16. The plant according to claim 15, wherein the synthesis loop is non-isobaric and said stripper and condenser operate at a pressure lower than the pressure of the reactor.

17. The plant according to claim 15, wherein the synthesis loop comprises a centrifugal pump arranged to feed the recycle solution from the condenser to the reactor, raising the pressure of the solution to the reaction pressure.

18. A method for revamping a urea plant, wherein:
    the plant comprises:
    a reactor where $CO_2$ and $NH_3$ react at a reaction pressure to form an aqueous solution of urea;
    a stripper fed with said aqueous solution of urea, wherein the solution is treated at a stripping pressure obtaining a purified solution and a gaseous phase containing ammonia and carbon dioxide and wherein the stripper includes a falling-film vertical tube bundle;

a condenser for condensing said gaseous phase from the stripper at a condensation pressure to form a recycle solution which is sent back to the reactor, thus forming a synthesis loop;

a steam system comprising at least a first steam line arranged to produce a first steam flow using heat removed from the condenser, wherein said first steam flow is used as a heat source in at least one downstream section of the plant;

and the method includes:

adding a steam compressor to said steam system, the added compressor being arranged to raise the pressure of said first steam flow, wherein the added compressor is driven by an electric motor.

19. The process according to claim 4, wherein said condensation pressure is 80 bar or about 80 bar.

20. The process according to claim 10, wherein the reaction pressure is greater than 200 bar.

21. The plant according to claim 15, wherein the synthesis loop is non-isobaric and said stripper and condenser operate at a pressure at least 20 bar lower than the pressure of the reactor.

\* \* \* \* \*